(12) United States Patent
Everett et al.

(10) Patent No.: US 8,137,273 B2
(45) Date of Patent: Mar. 20, 2012

(54) SYSTEMS AND METHODS FOR INTEGRATING HEMODYNAMIC AND IMAGING EXAMINATIONS

(75) Inventors: Deborah Ann Everett, Clayton, NC (US); Bruce Friedman, Jasper, GA (US); Paul Lawrence Mullen, Waukesha, WI (US); William Alphonsus Zang, Cedarburg, WI (US)

(73) Assignee: General Electric Company, Schenectady, NY (US)

( * ) Notice: Subject to any disclaimer, the term of this patent is extended or adjusted under 35 U.S.C. 154(b) by 311 days.

(21) Appl. No.: 12/362,942

(22) Filed: Jan. 30, 2009

(65) Prior Publication Data

US 2010/0198062 A1 Aug. 5, 2010

(51) Int. Cl.
*A61B 8/00* (2006.01)
(52) U.S. Cl. .................. 600/437; 600/485; 600/500
(58) Field of Classification Search .............. 600/500, 600/485, 463, 437, 407, 454, 486, 490
See application file for complete search history.

(56) References Cited

U.S. PATENT DOCUMENTS

| | | | |
|---|---|---|---|
| 5,630,424 A | 5/1997 | Raines et al. | |
| 5,718,232 A | 2/1998 | Raines et al. | |
| 6,017,307 A | 1/2000 | Raines | |
| 6,149,587 A | 11/2000 | Raines | |
| 6,152,881 A | 11/2000 | Raines et al. | |
| 7,172,555 B2 | 2/2007 | Poliac et al. | |
| 7,214,192 B2 | 5/2007 | Poliac et al. | |
| 2002/0002339 A1* | 1/2002 | Sugo et al. | 600/485 |
| 2005/0143640 A1* | 6/2005 | Hoctor et al. | 600/407 |
| 2005/0154299 A1* | 7/2005 | Hoctor et al. | 600/437 |
| 2006/0058660 A1* | 3/2006 | Sandy et al. | 600/437 |
| 2007/0225606 A1 | 9/2007 | Naghavi et al. | |
| 2007/0238995 A1 | 10/2007 | Sui et al. | |
| 2008/0039722 A1 | 2/2008 | Mejia et al. | |
| 2010/0285082 A1* | 11/2010 | Fernandez | 424/422 |

OTHER PUBLICATIONS

Unetixs, MultiLab Series II LHS-IMG, retrieved from the internet on Jan. 28, 2009 via URL: http://www.unetixs.com/multilab-2-lhs-img.html.

* cited by examiner

*Primary Examiner* — Tse Chen
*Assistant Examiner* — Joel F Brutus
(74) *Attorney, Agent, or Firm* — The Small Patent Law Group; Dean D. Small

(57) ABSTRACT

Hemodynamic data and imaging data are obtained about a patient, and the data is combined to generate a single report integrating same. While a hemodynamic system obtains the hemodynamic data, an imaging system obtains the imaging data. Preferably, the report confirms the absence or presence (and/or severity) of peripheral arterial disease, including quantitative data. The hemodynamic system and the imaging system can communicate directly, indirectly, and/or wirelessly. They may be contained within a common enclosure and/or integrated into a single apparatus. Either or both of the hemodynamic system and/or the imaging system can also be configured to measure the blood pressure of the patient. Preferably, the imaging system is an ultrasound imaging system, and improved workflows for diagnosing peripheral arterial disease result.

23 Claims, 3 Drawing Sheets

SYSTEMS AND METHODS FOR INTEGRATING HEMODYNAMIC AND IMAGING EXAMINATIONS

CROSS-REFERENCE(S) TO RELATED APPLICATION(S)

Not applicable.

STATEMENT REGARDING FEDERALLY SPONSORED RESEARCH OR DEVELOPMENT

Not applicable.

REFERENCE(S) TO MICROFICHE APPENDIX AND/OR COPYRIGHT PROTECTION

Not applicable.

BACKGROUND

1. Field

In general, the inventive arrangements relate to medical systems, and more specifically, to integrating hemodynamic and imaging systems.

2. Description of Related Art

Hemodynamics involve the flow of blood in living animals. Factors influencing hemodynamics include, for example, CO, circulating fluid volumes, respiration, vascular diameter, resistance, and/or blood viscosity. Each of these factors may, in turn, be influenced by physiological factors, such as, for example, a person's weight, diet, exercise, health, sickness, and/or disease, as well as any medications, drugs, and/or alcohol that a person may be using. Understanding a person's hemodynamic condition often depends on measuring the person's blood flow at different points along the person's blood circulation.

Ultrasound, on the other hand, is, among other things, a diagnostic medical imaging technique, and it is often used to visualize, for example, muscles, tendons, and/or internal organs of a person. Other imaging techniques can include, for example, medical imaging equipment for general radiology, functional imaging, molecular imaging, vascular imaging, fluoroscopy, mammography, neurology, oncology, radio pharmacology, x-ray, computed tomography (CT), nuclear medicine (NM), positron emission tomography (PET), magnetic resonance imaging (MRI), and/or photoplethysmography. While the present inventive arrangements will be described in particular terms of ultrasound medical imaging, they are not limited in this regard.

Now then, previous hemodynamic and imaging systems are separate and disparate systems, as will be elaborated upon.

It is estimated that in North America and Europe, approximately 27 million people suffer from peripheral arterial disease (PAD)—which is also known as peripheral vascular disease (PVD) and/or peripheral artery occlusive disease (PAOD). It is often caused by the obstruction of large arteries in a person's arms and/or legs. PAD can often result from atherosclerosis, inflammatory processes leading to stenosis, an embolism, and/or thrombus formation. Often, it causes acute and/or chronic ischemia (i.e., lack of blood supply), often in a person's legs. Moreover, the prevalence of PAD in people aged over 55 years is approximately 10-25%, and it increases with age. Approximately 70-80% of affected individuals are asymptomatic, while others are symptomatic. Typical symptoms of PAD can include any of the following: calf pain in either or both leg(s), particularly while walking or running; painful sensations and/or tingling in the feet; or numbness and/or loss of feeling in a person's limbs (e.g., arms and/or legs).

As a result, early detection and monitoring of PAD is of growing importance, particularly in order to be able to provide early treatment to patients, including to general aging populations and older demographics, as is typical in many countries, including the U.S. In general, detecting PAD usually involves evaluating the arteries that supply blood to lower body extremities.

Upon initial suspicion of symptomatic PAD, a common first examination is used to determine a patient's ankle brachial pressure index (ABPI or ABI), which measures a fall in blood pressure in the arteries supplying blood to the person's legs, particularly relative to the person's arms. Ideally, ABPIs should be at least 1. Reduced ABPIs (e.g., less than 0.9) can be consistent with the on-set of PAD, while values of ABPI less than 0.8 can indicate moderate disease. ABPIs less than 0.5 can indicate severe disease. Such determinations are often referred to as "indirect" assessments, and they are conducted by techniques such as measuring a patient's blood pressure, segmental limb pressure, toe pressure, pulse volume readings (PVR), exercise stress levels, blood oxygen concentrations (aka oximetry and/or pulse oximetry), and/or cutaneous temperatures. Many of these tests are conducted in special environments, such as a doctor's office, hospital, and/or other medical facilities. The tests carried out by such hemodynamic systems often require attaching sensors to the patient at various locations on the patient's body.

Now then, if a patient's hemodynamic readings are abnormal and/or otherwise merit additional consideration, a common next step involves conducting a lower limb Doppler ultrasound examination of the patient's legs, particularly in order to more closely examine a site and extent, if any, of atherosclerosis at the femoral artery. Such determinations are often referred to as "direct" assessments, and they are often conducted by techniques such as duplex imaging, typically through the use of hemodynamic evaluation with Doppler interrogation and ultrasound imaging. Many duplex ultrasound systems include both high and low frequency imaging capabilities, as well as both audible and spectral Doppler evaluation for high and low frequency evaluations.

One of the difficulties in using two different and independent systems, as described above (e.g., one for hemodynamic assessment, and another for ultrasound and/or other imaging), however, is that both systems are often needed for a single patient. For example, one clinician may use a hemodynamic system to provide an initial diagnosis of PAD, while another may then use an ultrasound imaging system to further the analysis—such that the two systems are used independently and separately, and oftentimes by different caregivers. Moreover, the two different tests may require the patient to have two or more separate appointments, perhaps on different dates. The patient could also be required to move between healthcare rooms and/or facilities for the different tests. The equipment could also need to be moved from one patient's room to another patient's room, bringing in the hemodynamic system first, followed by the ultrasound (or other imaging system) next—or vice versa. This can lead to disadvantages of, among other things, wasting space, time, cost, capitol equipment allocations, as well as personnel and/or other inefficiencies. As a result, it is not uncommon for caregivers to chose only one of direct assessment or indirect assessment as a matter of convenience and/or logistics, leading to compromised patient exam quality. Accordingly, at least one or more of patients, healthcare providers, and/or healthcare facilities are thereby inconvenienced.

Moreover, when both systems are utilized on a single patient, the data generated from the separately utilized systems is received separately, evaluated separately, and provided in separate reports. Accordingly, a single, integrated report combining the findings of the hemodynamic system and the imaging system would be advantageous. Moreover, the amount of time required to carry out and process separate testing systems is considerable.

As a result of at least the foregoing, it would be advantageous to have an overall integrated system that combines patient workflows and medical evaluations from hemodynamic and imaging systems, such as ultrasound imaging systems, particularly for monitoring PAD. And a single, comprehensive report that combines data from both systems would also be advantageous for patients, healthcare providers, and/or healthcare facilities.

SUMMARY

In one embodiment, an integrated medical system comprises a hemodynamic system, an imaging system, and a processor. The hemodynamic system obtains hemodynamic data about a patient, such as the patient's blood pressure, while the imaging system obtains imaging data about the patient, such as ultrasound imagery of the patient. The processor then combines the hemodynamic data and the imaging data into a single report integrating same. Either one or both of the hemodynamic system and/or the imaging system can be used to measure the blood pressure of the patient. Preferably, the imaging system is an ultrasound imaging system, and the hemodynamic system and the imaging system can communicate directly, indirectly, and/or wirelessly. In various embodiments, they may be contained within a common enclosure and/or integrated into a single apparatus, and the report preferably reflects a peripheral arterial disease condition of the patient. Thus, wherein the hemodynamic data and the imaging data are obtained about the patient, they are combined into the single report integrating same. When combining the hemodynamic data and the imaging data, the hemodynamic data can be transmitted to the imaging system and/or vice-versa—i.e., the imaging data can be transmitted to the hemodynamic system. They can be transmitted therebetween directly, indirectly, and/or wirelessly. Improved workflows for diagnosing peripheral arterial disease result.

BRIEF DESCRIPTION OF SEVERAL VIEWS OF THE DRAWINGS

A clear conception of the advantages and features constituting inventive arrangements, and of various construction and operational aspects of typical mechanisms provided by such arrangements, are readily apparent by referring to the following illustrative, exemplary, representative, and non-limiting figures, which form an integral part of this specification, in which like numerals generally designate the same elements in the several views, and in which.

DETAILED DESCRIPTION OF PREFERRED EMBODIMENTS

Referring now to the figures, preferred embodiments of the inventive arrangements will be described in terms of hemodynamic monitoring and ultrasound imaging systems. However, the inventive arrangements are not limited in this regard. For example, while variously described embodiments may provide ultrasound imaging systems in a diagnostic context, other contexts are also hereby contemplated, including various other imaging techniques, and/or the like.

Figure 1:
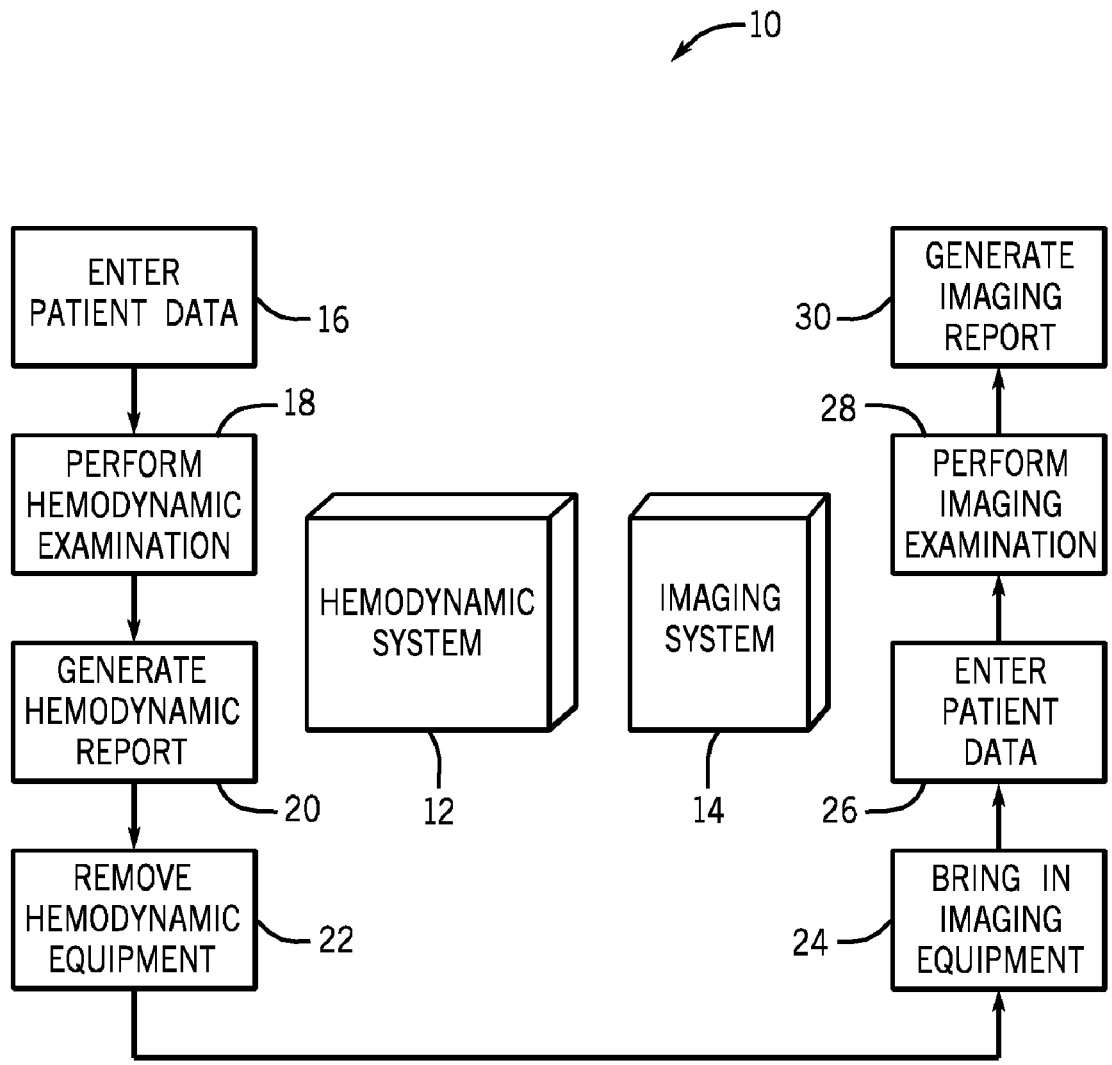
FIG. 1 illustrates a prior art schematic view of a common workflow procedure used to diagnose peripheral arterial disease (PAD) in a patient.

Now then, referring to FIG. 1, there is shown a prior art schematic view of a common workflow procedure 10 used to diagnose peripheral arterial disease (PAD) in a patient (not shown). More specifically, both a hemodynamic system 12 and an imaging system 14, such as an ultrasound imaging system, are used to diagnose PAD in the patient. As shown, however, both the hemodynamic system 12 and the imaging system 14 are separate systems, with no connections therebetween—physical, electronic, and/or otherwise.

As can be seen, a healthcare provider (not shown) enters patient data into the hemodynamic system 12 at a first step 16, after which a hemodynamic examination is performed on the patient at a next step 18, particularly using hemodynamic equipment, such as the hemodynamic system 12. At a next step 20, the hemodynamic system 12 (and/or other) is used to generate a hemodynamic report—after which it is assumed, for the present purposes, that an imaging examination is also desired, and so the hemodynamic equipment is removed from the patient's presence at a next step 22. At a next step 24, imaging equipment, such as the imaging system 14, is brought into the patient's presence, particularly for an imaging examination, such as an ultrasound examination. Accordingly, another healthcare provider (not shown), such as an ultrasound sonographer, which may or may not be the same as the initial healthcare provider, again enters (and/or re-enters) patient data into the imaging system 14 at a next step 26, after which an imaging examination is performed on the patient at a next step 28, particularly using the imaging equipment, such as the imaging system 14. At a final step 30, the imaging system 14 (and/or other) is used to generate an imaging report, after which the hemodynamic report and imaging report are separately used to evaluate the presence and/or condition of PAD in the patient.

As previously described, common hemodynamic examinations may include blood pressure screenings, ECG monitoring, measuring blood oxygenation, and/or the like. Similarly, common imaging examinations may include ultrasound imaging examinations, commonly used, in this context, for example, to image a portion of the patient's arterial systems and/or determine the person's blood flow velocities. Accordingly, the hemodynamic report contains hemodynamic data, as does the separate imaging report contain imaging data, which, when taken together, can be used to diagnose the patient's PAD condition.

As described at step 22, the hemodynamic equipment is moved, for example, out of the patient's room (not shown), to be stored and/or used at another location (not shown). Alternatively, the patient could, of course, also physically move to another room (not shown), and/or the like, so that the patient is no longer in the presence of (or at least proximate to) the hemodynamic equipment at step 22. As a result, the imaging equipment is then, for example, brought into the patient's room (and/or the patient otherwise moves theretowards), as described at step 24, where it can be set up proximate to the patient for the imaging examination. As described, patient data is entered separately at steps 16 and 26 for the respective hemodynamic system 12 and imaging system 14.

As is evident from the workflow procedure 10 of FIG. 1, redundant functions are performed by the caregiver(s), and the end result generates two separate reports, both providing data as to the potential incidence of PAD in the patient. It is estimated that the completion of such a workflow procedure 10, from start to finish, averages approximately 72 minutes per patient.

As a result of the afore-mentioned cost and time constraints, often only a hemodynamic examination or imaging examination is chosen. However, both direct assessments and indirect assessments have limitations. Accordingly, patient exam quality is compromised. However, when both direct assessments and indirect assessments are deployed, they offer the patient an optimal evaluation and a more accurate overall assessment.

Figure 2:
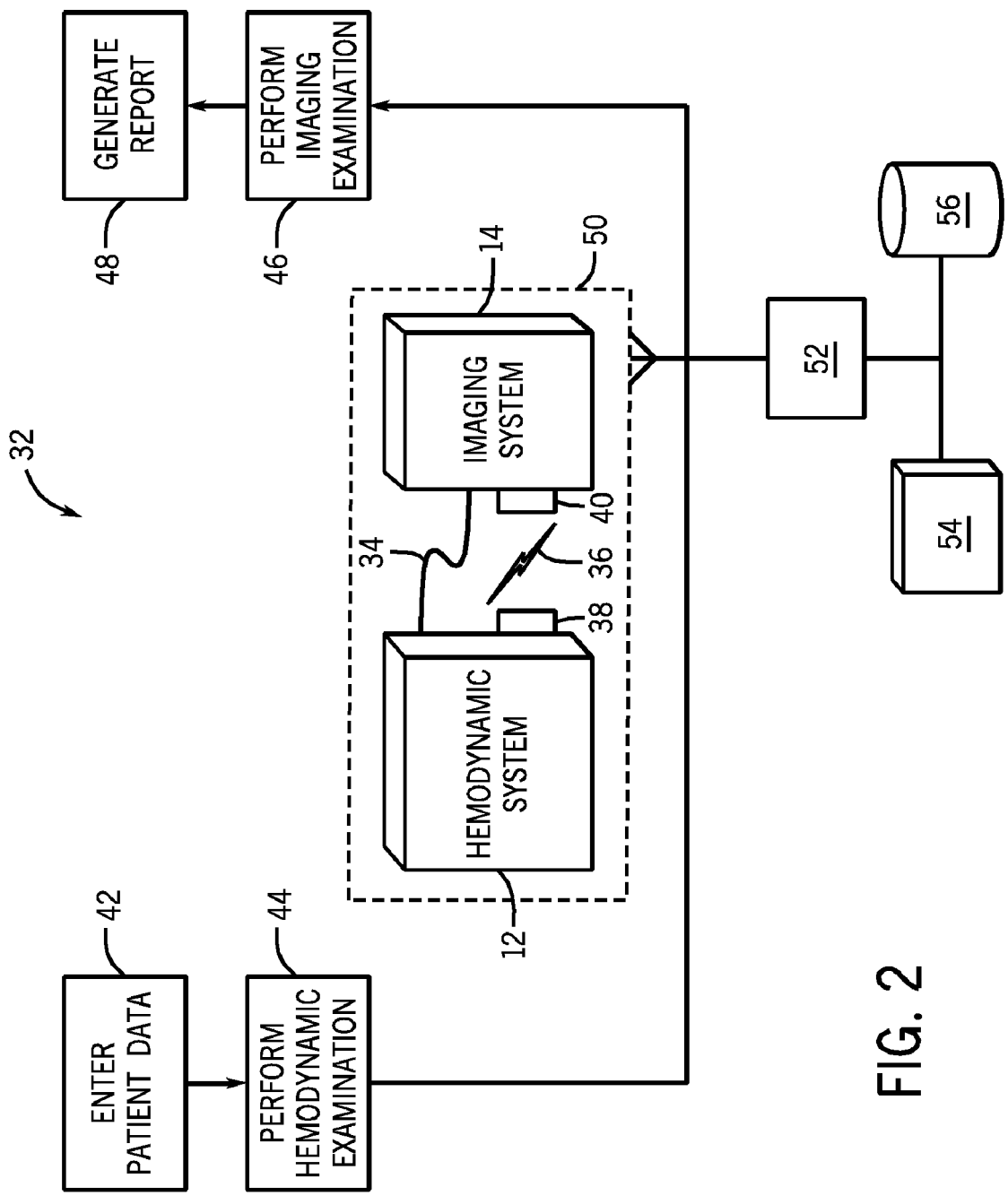
FIG. 2 illustrates a novel schematic view of an improved workflow procedure used to diagnose PAD in a patient, in particular accord with the inventive arrangements.

Referring now to FIG. 2, there is shown a novel schematic view of an improved workflow procedure 32 used to diagnose PAD in the patient (not shown). More specifically, the hemodynamic system 12 and the imaging system 14, such as an ultrasound imaging system, are again used to diagnose PAD in the patient. As shown, however, the hemodynamic system 12 and the imaging system 14 now communicate with one another using, for example, a direct connection 34, such as a serial cable, parallel cable, fiber optic ink, USB port, LAN line, and/or the like. In another embodiment, the hemodynamic system 12 and the imaging system 14 communicate with one another using, for example, an indirect and/or wireless connection 36, particularly using, for example, transceivers 38, 40 (and/or the like) respectively supported by both systems 12, 14. In either event, the hemodynamic data is made available to the imaging system 14, and/or vice versa—i.e., the imaging data is made available to the hemodynamic system 12.

As can be seen, the healthcare provider (not shown) enters patient data into either the hemodynamic system 12 or the imaging system 14 (or other) at a first step 42, after which a hemodynamic examination is performed on the patient at a next step 44, particularly using hemodynamic equipment, such as the hemodynamic system 12—after which it is assumed, for the present purposes, that an imaging examination is also desired, and so an imaging examination is performed on the patient at a next step 46, particularly using the imaging equipment, such as the imaging system 14. Both systems 12, 14 were made available to the healthcare provider at a single opportunity during a single evaluation/examination. Then, at a final step 48, a combined hemodynamic report and imaging report is generated to be used to evaluate the presence and/or condition of PAD in the patient. As can be seen, the patient data only needs to be entered once, at step 42, and not repeatedly as with the workflow procedure 10 of FIG. 1, particularly since the hemodynamic system 12 and the imaging system 14 are now in communication with each other through the direct connection 34 or indirect and/or wireless connection 36. Thus, once the patient data is entered a single time, such as at step 42, it is then shared by both the hemodynamic system 12 and the imaging system 14.

As such, patient exams can be performed on the patient in any particular order (i.e., either the hemodynamic examination first or the imaging examination first), and the tests for diagnosing PAD can include both those for an indirect evaluation, as well as for a direct evaluation—i.e., tests carried out, respectively, by the hemodynamic system 12 as well as by the imaging system 14. In addition, at the conclusion of the workflow procedure 32, a comprehensive report is generated including both the hemodynamic data from the hemodynamic examination and the imaging data from the imaging examination.

As in FIG. 1, common hemodynamic examinations may include blood pressure screenings, ECG monitoring, measuring blood oxygenation, and/or the like. Similarly, common imaging examinations may include ultrasound imaging examinations, commonly used, in this context, for example, to image a portion of the patient's arterial systems and/or determine the person's blood flow velocities. Accordingly, the combined report contains hemodynamic data and imaging data, which can be used to diagnose the patient's PAD condition.

Since the hemodynamic system 12 and the imaging system 14 now communicate via the direct connection 34 and/or indirect and/or wireless connection 36, the need to separately enter patient data for each system is thereby eliminated (see, e.g., steps 16 and 26 in FIG. 1). In addition, if the hemodynamic system 12 and the imaging system 14 are brought together under a common platform 50, the need to remove the hemodynamic equipment from the patient's presence and separately bring the imaging equipment into the patient's presence is also thereby eliminated (see, e.g., steps 22 and 24 in FIG. 1).

As is evident from comparing the workflow procedure 10 of FIG. 1 and the workflow procedure 32 of FIG. 2, performing redundant functions by separate caregivers is eliminated, and the end result generates one report, not two, providing comprehensive data as to the potential incidence of PAD in the patient. It is estimated that the completion of such a workflow procedure 32, from start to finish, averages approximately 48 minutes per patient—or substantially less than the workflow procedure 10 of FIG. 1. Thus, a diagnosis can be completed with more efficiency, cost effectiveness, and greater accuracy.

In accord with the inventive arrangements, at least one or more of the hemodynamic system 12, imaging system 14, and/or common platform 50 includes a processor 52 that receives the hemodynamic data obtained by the hemodynamic system 12, as well as the imaging data obtained by the imaging system 14. The processor 52 combines the data into an integrated data set that combines both the hemodynamic data and the imaging data and that can be printed out by a printer 54 to provide a combined, comprehensive report on the patient's PAD condition, particularly including both sets of data. As a further option, particularly in connection with, or as a supplement to, the printer 54, the combined data from the hemodynamic system 12 and the imaging system 14 can also be sent to and/or stored at a central data site 56 within the health care facility (not shown) and/or otherwise (not shown).

Figure 3A:
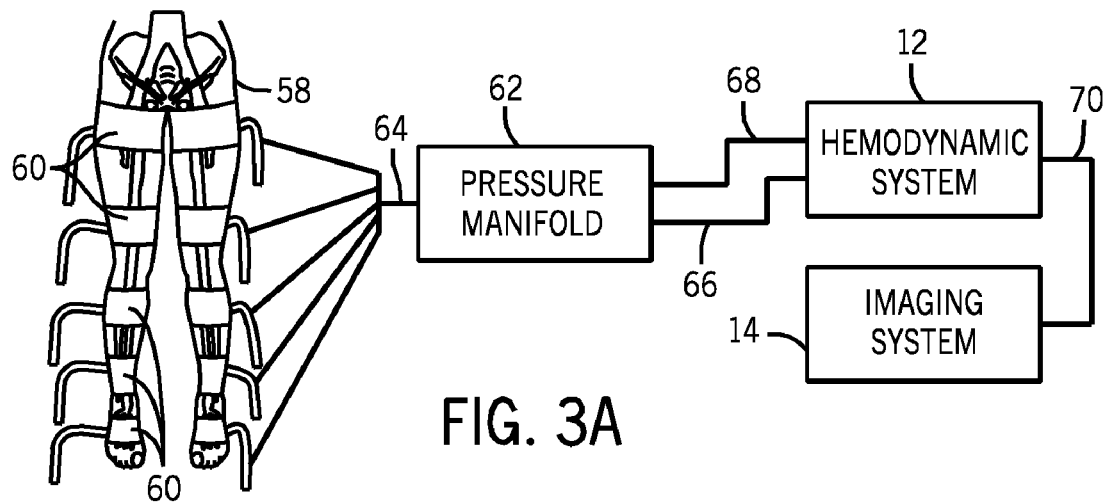
FIGS. 3A-3C illustrate alternative novel systems used to diagnose PAD in a patient, again in particular accord with the inventive arrangements.
Figure 3B:
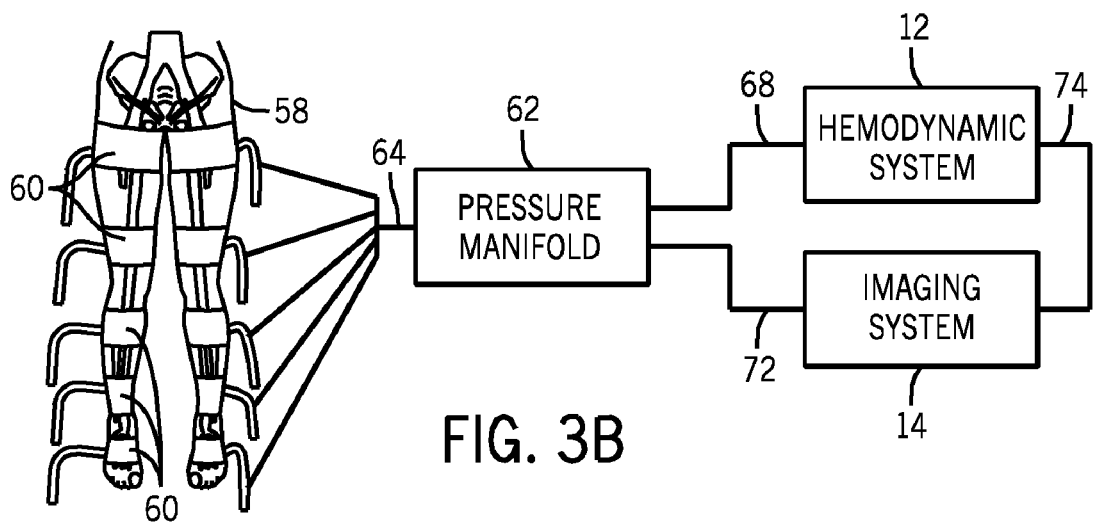
Figure 3C:
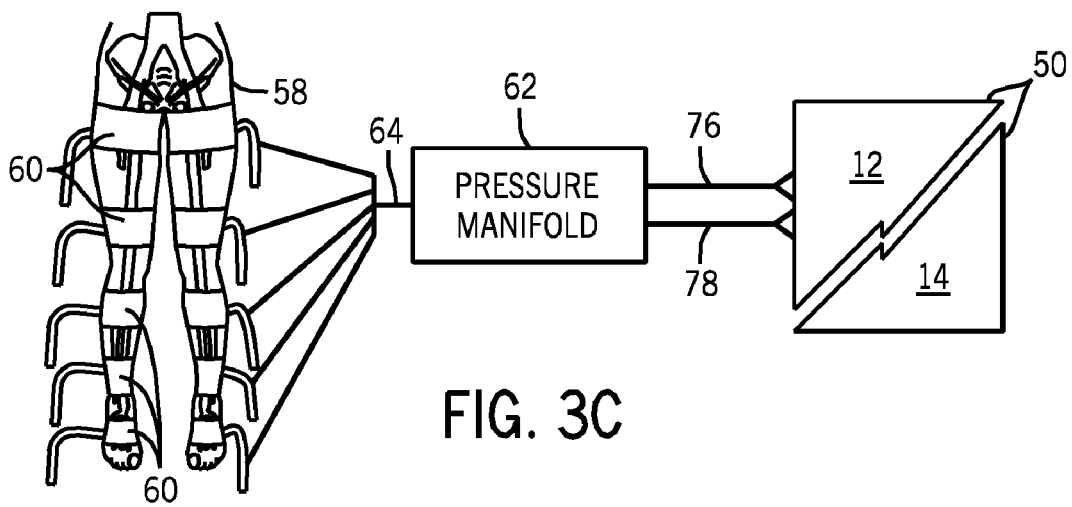

Referring now to FIGS. 3A-3C, there are shown differing exemplary embodiments illustrating additional use of the inventive arrangements. As such, there can be seen in the figures, for example, a patient's legs 58 having a plurality of blood pressure cuffs 60 displaced along the length of the legs 58. A pressure manifold 62 is provided to pressurize and depressurize the blood pressure cuffs 60 via one or more conduit(s) 64 connected therebetween the blood pressure cuffs 60 and the pressure manifold 62.

In the embodiment depicted in FIG. 3A, the hemodynamic system 12 controls the pressure in the pressure manifold 62 through a link 66, and it thus controls inflation and deflation of the blood pressure cuffs 60 via the one or more conduit(s) 64. The pressures detected by the inflation and deflation of the blood pressure cuffs 60 are detected by the hemodynamic system 12 via a feedback link 68. Accordingly, in this embodiment, the hemodynamic system 12 controls the pressures in the blood pressure cuffs 60, and it also detects the pressures therewithin. A link 70 then communicates the hemodynamic pressure data to the imaging system 14, whereby the hemodynamic data is combined with data obtained by the imaging system 14, so as to diagnose the PAD condition of the patient (not shown in fall). The link 70 can be either a direct connection 34 or indirect and/or wireless connection 36 (e.g., see FIG. 2). As such, the hemodynamic data is communicated to the imaging system 14 via the link 70, whereby it is preferably integrated with the image data gathered by the imaging system 14, and preferably combined together therewith to produce an integrated and/or comprehensive report detailing both the hemodynamic data and the imaging data.

In the embodiment depicted in FIG. 3B, the imaging system 14 controls the pressure in the pressure manifold 62 through a link 72, and it thus controls inflation and deflation of the blood pressure cuffs 60 via the one or more conduit(s) 64. The pressures detected by the inflation and deflation of the blood pressure cuffs 60 are again detected by the hemodynamic system 12 via the feedback link 68. Accordingly, in this embodiment, the imaging system 14 controls the pressures in the blood pressure cuffs 60, but the hemodynamic system 12 detects the pressures therewithin. A link 74 then communicates the hemodynamic pressure data to the imaging system 14, whereby the hemodynamic data is combined with data obtained by the imaging system 14, so as to diagnose the PAD condition of the patient (not shown in full). The link 74 can be either a direct connection 34 or indirect and/or wireless connection 36 (e.g., see FIG. 2). As such, the hemodynamic data is communicated to the imaging system 14 via the link 74, whereby it is preferably integrated with the image data gathered by the imaging system 14, and preferably combined together therewith to produce an integrated and/or comprehensive report detailing both the hemodynamic data and the imaging data.

In the embodiment depicted in FIG. 3C, the hemodynamic system 12 and the imaging system 14 are combined into the common platform 50. Accordingly, the combined platform 50 contains the full functionality of both the hemodynamic system 12 and the imaging system 14. As such, it again controls the pressure in the pressure manifold 62 through a link 76, and it thus controls inflation and deflation of the blood pressure cuffs 60 via the one or more conduit(s) 64. The pressures detected by the inflation and deflation of the blood pressure cuffs 60 are detected by the common platform 50 via a feedback link 78. Accordingly, in this embodiment, the common platform 50 controls the pressures in the blood pressure cuffs 60, and it also detects the pressures therewithin. Since the hemodynamic system 12 and the imaging system 14 are combined into the common platform 50, a further link (e.g., link 70 in FIG. 3A and/or link 74 in FIG. 3B) is either unnecessary and/or internal therewithin, whereby the hemodynamic data is combined with data obtained by the imaging system 14, so as to diagnose the PAD condition of the patient (not shown in fall). As such, the hemodynamic data is preferably integrated with the image data gathered by the imaging system 14, and preferably combined together therewith to produce an integrated and/or comprehensive report detailing both the hemodynamic data and the imaging data.

As described in the embodiment depicted in FIG. 3C, it can be seen that the hemodynamic system 12 and the imaging system 14 have been physically incorporated into the common platform 50, creating a single integrated system that includes the functions of both the hemodynamic system 12 and the imaging system 14 in a single apparatus within a common enclosure, such that both systems 12, 14 are transportable, for example, together as an integrated apparatus via the common platform 50. They can be contained within a common enclosure and/or integrated into a single apparatus.

In accordance with the foregoing, one technical effect is to combine a hemodynamic system 12 with an imaging system 14 into a common platform 50 to improve PAD diagnosis workflow 32 for patients, healthcare providers, and/or healthcare facilities.

Accordingly, it should be readily apparent that this specification describes illustrative, exemplary, representative, and non-limiting embodiments of the inventive arrangements. Accordingly, the scope of the inventive arrangements are not limited to any of these embodiments. Rather, various details and features of the embodiments were disclosed as required. Thus, many changes and modifications—as readily apparent to those skilled in these arts—are within the scope of the inventive arrangements without departing from the spirit hereof, and the inventive arrangements are inclusive thereof Accordingly, to apprise the public of the scope and spirit of the inventive arrangements, the following claims are made:

What is claimed is:

1. An integrated medical system, comprising:
a blood pressure measuring system for obtaining hemodynamic data about a patient;
a hemodynamic system configured to receive the hemodynamic data and generate a hemodynamic report;
an imaging system configured to obtain imaging data about the patient and generate an image of the patient, the hemodynamic system and the imaging system combined into a common platform, at least one of the hemodynamic system or the imaging system controlling an operation of the blood pressure measuring system; and
a processor configured to receive the hemodynamic data and the imaging data and combine the hemodynamic data and the imaging data together to generate a report integrating the hemodynamic report and the image, wherein the hemodynamic system and the imaging system are configured to communicate independently of the generated report integrating the hemodynamic report and the image.

2. The integrated medical system of claim 1, wherein the blood pressure measuring system includes one or more blood pressure cuffs configured to be affixed to the patient to measure said blood pressure.

3. The integrated medical system of claim 1, wherein the blood pressure measuring system includes one or more blood pressure cuffs, a pressure in the blood pressure cuffs controlled, at least in part, by the hemodynamic system.

4. The integrated medical system of claim 1, wherein the blood pressure measuring system includes one or more blood pressure cuffs, a pressure in the blood pressure cuffs controlled, at least in part, by the imaging system.

5. The integrated medical system of claim 1, wherein the imaging system is an ultrasound imaging system.

6. The integrated medical system of claim 1, wherein the hemodynamic system and the imaging system are configured to communicate directly.

7. The integrated medical system of claim 1, wherein the hemodynamic system and the imaging system are configured to communicate indirectly.

8. The integrated medical system of claim 1, wherein the hemodynamic system and the imaging system are configured to communicate wirelessly.

9. The integrated medical system of claim 1, wherein both the hemodynamic system and the imaging system are contained within a common enclosure.

10. The integrated medical system of claim 1, wherein both the hemodynamic system and the imaging system are integrated into a single apparatus that is independent of the processor and the blood pressure measuring system.

11. The integrated medical system of claim 1, wherein the report integrating the hemodynamic data and the imaging data reflects a peripheral arterial disease condition of the patient.

12. The integrated medical system of claim 1 further comprising a pressure manifold to control a pressure in the blood pressure measuring system, the pressure manifold controlled by at least one of the hemodynamic system or the imaging system.

13. The integrated medical system of claim 1, wherein at least one of the hemodynamic system or the imaging system directly controls the blood pressure measuring system independent of the processor.

14. The integrated medical system of claim 1, wherein the hemodynamic system controls the blood pressure measuring system based on the hemodynamic data received at the hemodynamic system.

15. The integrated medical system of claim 1, wherein the imaging system receives the blood pressure data from the blood pressure monitoring system and controls the blood pressure measuring system based on at least one of the hemodynamic data or the imaging data.

16. A method of monitoring a medical condition of a patient, comprising:
 controlling a blood pressure measuring system with at least one of a hemodynamic system or an imaging system that are combined into a common platform;
 obtaining hemodynamic data about a patient with the hemodynamic system;
 obtaining imaging data about the patient with the imaging system; and
 combining the hemodynamic data and the imaging data into a report integrating the hemodynamic data and the imaging data, wherein the hemodynamic system and the imaging system are configured to communicate independently of the generated report.

17. The method of claim 16, wherein obtaining the hemodynamic data comprises measuring a blood pressure of the patient with the blood pressure measuring system.

18. The method of claim 16, wherein obtaining the imaging data comprises obtaining at least one ultrasound image of the patient.

19. The method of claim 16, wherein the report integrating the hemodynamic data and the imaging data reflects a peripheral arterial disease condition of the patient.

20. The method of claim 16, wherein combining the hemodynamic data and the imaging data comprises transmitting the hemodynamic data to an imaging system configured to obtain the imaging data.

21. The method of claim 20, wherein the hemodynamic data is transmitted to the imaging system one of directly, indirectly, or wirelessly.

22. The method of claim 16, wherein combining the hemodynamic data and the imaging data comprises transmitting the imaging data to a hemodynamic system configured to obtain the hemodynamic data.

23. The method of claim 22, wherein the imaging data is transmitted to the hemodynamic system one of directly, indirectly, or wirelessly.

* * * * *